(12) United States Patent
Samant et al.

(10) Patent No.: US 10,329,235 B2
(45) Date of Patent: Jun. 25, 2019

(54) SYSTEM AND METHOD FOR PRODUCING 1,4-CYCLOHEXANEDIMETHANOL AND 1,4-CYCLOHEXANEDICARBOXYLIC ACID FROM TEREPHTHALIC ACID

(71) Applicant: ClearWaterBay CHDM Technology Limited, New Territories (HK)

(72) Inventors: Ketan D. Samant, Glendora, CA (US); Drow Lionel O'Young, Walnut, CA (US); Yik Chung Chan, Hong Kong (CN)

(73) Assignee: ClearWaterBay CHDM Technology Limited, New Territories (HK)

( * ) Notice: Subject to any disclaimer, the term of this patent is extended or adjusted under 35 U.S.C. 154(b) by 0 days.

(21) Appl. No.: 15/693,403

(22) Filed: Aug. 31, 2017

(65) Prior Publication Data

US 2019/0062251 A1    Feb. 28, 2019

(51) Int. Cl.
*C07C 51/36* (2006.01)
*C07C 29/80* (2006.01)
*C07C 29/149* (2006.01)

(52) U.S. Cl.
CPC ............ *C07C 51/36* (2013.01); *C07C 29/149* (2013.01); *C07C 29/80* (2013.01); *C07C 2601/14* (2017.05)

(58) Field of Classification Search
CPC ....... C07C 51/36; C07C 29/149; C07C 29/80; C07C 2601/14
See application file for complete search history.

(56) References Cited

U.S. PATENT DOCUMENTS

| | | | |
|---|---|---|---|
| 2,917,549 A * | 12/1959 | Knowles | C07C 31/13 528/307 |
| 3,334,149 A | 8/1967 | Akin et al. | |
| 4,754,064 A | 6/1988 | Lillwitz | |
| 4,999,090 A | 3/1991 | Tateno et al. | |
| 5,118,841 A | 6/1992 | Cook et al. | |
| 5,202,475 A | 4/1993 | Cook et al. | |
| 5,387,752 A | 2/1995 | Scarlett et al. | |
| 5,395,987 A | 3/1995 | Rathmell et al. | |
| 5,552,512 A * | 9/1996 | Sublett | C08G 63/189 528/308 |
| 6,187,968 B1 | 2/2001 | Itoh et al. | |
| 6,291,706 B1 | 9/2001 | Sumner, Jr. et al. | |
| 6,294,703 B1 * | 9/2001 | Hara | B01J 23/96 502/25 |
| 6,495,730 B1 * | 12/2002 | Konishi | B01J 21/18 568/831 |
| 6,541,662 B2 | 4/2003 | Machida et al. | |
| 7,595,423 B2 | 9/2009 | Endou et al. | |
| 8,410,318 B2 | 4/2013 | Barton et al. | |
| 2002/0115884 A1 * | 8/2002 | Machida | C07C 51/36 562/400 |
| 2013/0030220 A1 | 1/2013 | Tennant | |

FOREIGN PATENT DOCUMENTS

| | | |
|---|---|---|
| CN | 102795967 B | 7/2015 |
| JP | 2002-69016 A | 3/2002 |
| JP | 2002-069032 * | 3/2002 |

OTHER PUBLICATIONS

JP2002-069032 translated (Year: 2002).*
International Search Report and Written Opinion in International Application No. PCT/US2018/048523, dated Nov. 9, 2018.

* cited by examiner

*Primary Examiner* — Jafar F Parsa
*Assistant Examiner* — Blaine G Doletski
(74) *Attorney, Agent, or Firm* — Nixon Peabody LLP

(57) ABSTRACT

This invention relates to the continuous production of 1,4-cyclohexane dimethanol (CHDM) and optionally and additionally of 1,4-cyclohexane dicarboxylic acid (CHDA) directly using terephthalic acid (TPA) as the raw material. More specifically, this invention relates to a method and system for continuous production of CHDM and CHDA that features direct use of TPA as feedstock, promotes efficient use of solvent and energy, and provides products with the desired high trans isomer content, by exploiting unexpected features of the thermodynamic phase behavior and the reaction mechanisms.

54 Claims, 8 Drawing Sheets

Figure 6

Preferred Water & Product Recirculation Flows

| Temperature (C) | Desired CHDA in Product (wt%) | Water/TPA Flow Ratio | Recirculation/TPA Flow Ratio |
|---|---|---|---|
| 150 | 50 | 1.04 | 99.67 |
|  | 40 | 1.55 | 145.66 |
|  | 30 | 2.42 | 203.83 |
|  | 20 | 4.15 | 273.11 |
| 160 | 50 | 1.04 | 76.92 |
|  | 40 | 1.55 | 108.57 |
|  | 30 | 2.42 | 147.01 |
|  | 20 | 4.15 | 190.33 |
| 170 | 50 | 1.04 | 59.42 |
|  | 40 | 1.55 | 81.37 |
|  | 30 | 2.42 | 105.61 |
|  | 20 | 4.15 | 131.28 |
| 180 | 50 | 1.04 | 46.12 |
|  | 40 | 1.55 |  |
|  | 30 | 2.42 |  |
|  | 20 | 4.15 | 90.42 |
| 190 | 50 | 1.04 | 35.23 |
|  | 40 | 1.55 |  |
|  | 30 | 2.42 |  |
|  | 20 | 4.15 | 60.29 |
| 200 | 50 | 1.04 | 26.63 |
|  | 40 | 1.55 | 32.51 |
|  | 30 | 2.42 | 38.98 |
|  | 20 | 4.15 | 44.23 |

Not Preferable
Preferable
More Preferable
Most Preferable

SYSTEM AND METHOD FOR PRODUCING 1,4-CYCLOHEXANEDIMETHANOL AND 1,4-CYCLOHEXANEDICARBOXYLIC ACID FROM TEREPHTHALIC ACID

FIELD OF THE INVENTION 1,4-cyclohexanedimethanol (hereinafter referred to as CHDM) is an important intermediate in the manufacture of polyester fibers, polyester resins, polycarbonates, and polyurethanes. It is particularly important when used as one of the diols in the manufacture of polyethylene terephthalate. Inclusion of CHDM in the polymer chains is effective in improving a wide range of useful properties such as toughness, heat resistance, weatherability, solvent resistance, and processability.

1,4-cyclohexanedicarboxylic acid (hereinafter referred to as CHDA) is a similarly important intermediate in the manufacture of synthetic fibers, synthetic resins, coatings, etc. Similar to CHDM, inclusion of CHDA in the polymer chains provides improved toughness, heat resistance, weatherability, etc.

Both CHDM and CHDA exist in cis and trans stereoisomeric forms. The trans isomers have much higher melting points than the cis isomers and CHDM and CHDA with high trans content are required to achieve many of the desirable polymer properties mentioned above.

This invention relates in general to the production of CHDM and CHDA by direct hydrogenation of terephthalic acid (hereinafter referred to as TPA). More specifically, by exploiting unexpected features of the thermodynamic phase behavior and the reaction mechanisms, this invention provides a method and system for producing CHDM and CHDA that features direct use of TPA as feedstock, promotes efficient use of water and energy, and provides products with the desired high trans isomer content.

BACKGROUND

TPA is the true raw material for production of CHDM and CHDA. Hydrogenation of the aromatic ring of TPA would give CHDA and hydrogenation of the aromatic ring as well as the carboxylic acid side-chains would give CHDM. This is as shown below:

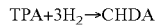

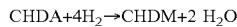

However, direct use of TPA in hydrogenation reactions is made complicated by its high melting point and poor solubility in reaction solvents (especially in water) at temperatures that are favorable to the hydrogenation reactions. As a result, instead of TPA, industrial processes for production of CHDM and CHDA rely on hydrogenation of derivatives of TPA that can be more easily used in liquid phase—in melt or in solution. This means that such processes have to include additional processing steps for first converting TPA to its desired derivatives—typically requiring high initial investment, increased energy consumption, and high operating costs.

For example, use of dimethyl terephthalate (a diester of TPA, hereinafter referred to as DMT), for production of CHDM is well known in prior art. Hydrogenation of DMT to CHDM typically proceeds in two stages—hydrogenation of the aromatic ring over palladium catalyst to get dimethyl 1,4-cyclohexanedicarboxylate (hereinafter referred to as DMCD) followed by hydrogenation of the ester side-chains of DMCD over copper and chromium based catalyst to get CHDM. The two reactions cannot be combined into one stage and the sequence of reaction steps cannot be changed as significant by-product formation occurs otherwise. Both stages can be carried out in gas-liquid-solid (hereinafter referred to as GLS) reactors as described, for example, in U.S. Pat. No. 3,334,149 (assigned to Eastman Kodak Company) and in U.S. Pat. No. 6,187,968 (assigned to SK NJC Co., Ltd.). The hydrogenation of DMCD can be carried out in vapor phase as described in U.S. Pat. Nos. 5,387,752 and 5,395,987 (assigned to Eastman Chemical Company). Preparation of DMT involves esterification of TPA with methanol at high pressures and temperatures that requires specialized, costly process equipment and also results in increased energy consumption and additional operating costs. Additionally, DMT must be separated and purified by distillation, to remove any byproducts and esterification catalysts, prior to its use in the hydrogenation stages. Also, hydrogenation of DMT creates methanol. Additional processing steps are therefore required for processing and purification of methanol so that it can be reused in the esterification process.

Process for producing CHDM from TPA is claimed in U.S. Pat. No. 8,410,318 (assigned to Eastman Chemical Company). However, this is highly misleading as the first stage of the claimed process involves esterification of TPA with (4-methylcyclohexyl) methanol (hereinafter referred to as MCHM) to produce the bis(4-methylcyclohexyl)methanol diester of TPA. This diester is then hydrogenated in two additional stages to CHDM. This in essence is similar to the DMT based process (the only difference being the use of MCHM instead of methanol to form the initial diester of TPA) and therefore suffers from the same aforementioned problems.

Processes for the production of CHDA using derivatives of TPA as feedstock are also known in the prior art. For example, U.S. Pat. Nos. 5,118,841 and 5,202,475 (assigned to Eastman Chemical Company) describe hydrogenation over ruthenium catalyst using aqueous solution of sodium salt of TPA. These processes not only require the additional step of preparing such salts, but also require treatment of the hydrogenation product with mineral acids in order to recover the CHDA product. Additionally, the sodium salts of mineral acids generated in the process also need to be disposed of.

Process for producing CHDM from CHDA or esters of CHDA is described in U.S. Pat. No. 6,294,703 (assigned to Mitsubishi Chemical Company). CHDM is produced by hydrogenation of aqueous solution of CHDA or diesters of CHDA in GLS reactors over catalyst comprising ruthenium, tin, and platinum at temperatures from 150-240° C. and pressures ranging 1-25 MPa. The amount of water used is preferably 1 to 10 fold by weight of the CHDA feed. This patent provides a route to CHDM starting from CHDA, but assumes the availability of CHDA and does not address the problems associated with production of CHDA from TPA or otherwise as noted above.

Based on this, it is clearly evident that it will be beneficial to have processes for production of CHDM and CHDA directly from TPA without going through an intermediate TPA derivative. As noted initially, the main hurdle for such processes is getting TPA into the liquid phase. TPA does not melt even at very high temperatures (sublimates above 300° C.) and its solubility in suitable reaction solvents is very poor. For example, solubility of TPA in water and the amount of water required for complete dissolution of TPA are listed below (water is a natural choice for reaction solvent as it is also a product of the hydrogenation of carboxylic acid side-chains):

| Temperature (° C.) | TPA Solubility (wt fraction) | Water for Complete Dissolution (wt Water:wt TPA) |
|---|---|---|
| 150 | 0.0022 | 456:1 |
| 200 | 0.016 | 61:1 |
| 250 | 0.11 | 9:1 |

Note that solubility increases as temperature increases. However, temperatures greater than 200° C. are highly undesirable due to significant by-product formation through decarboxylation and decarbonylation reactions.

Hydrogenation of aqueous slurries of phthalic acids to cyclohexanedicarboxylic acids has been studied in prior art. U.S. Pat. No. 4,754,064 (assigned to Amoco Corporation) describes use of rhodium catalyst in presence of recycled product and U.S. Pat. No. 6,291,706 (assigned to Eastman Chemical Company) describes the use of palladium catalyst. However, such processes as described are limited to batch operation such that TPA solids gradually dissolve in the solution just as the dissolved TPA gets hydrogenated to CHDA. Extending them to continuous operation would require the use of slurry GLS reactors with TPA as well as the catalyst in the solid phase. This is extremely problematic because high residence times and large equipment sizes are required, dissolution of TPA is not guaranteed even at high residence times, expensive filters are needed for separation of catalyst from reaction product, and TPA particles can block catalyst pores and also increase the attrition.

Continuous operation of TPA hydrogenation using fixed beds of catalyst is possible only if TPA is completely dissolved in the solvent. Due to its poor solubility, this would mean that the amount of solvent required is several hundred times the amount of TPA by weight. Reaction mixtures with such large amounts of solvent make the equipment sizes, catalysts requirements, and initial investment prohibitively high. Also, due to high purity requirements and stereo-isomeric nature of the CHDA and CHDM (this is explained below), the hydrogenation product eventually has to be completely separated from the solvent. This leads to very high energy costs, especially when water is the solvent due to high heat of vaporization of water.

U.S. Pat. No. 6,541,662 (assigned to Mitsubishi Gas Chemical Company, Inc.) describes a continuous process for producing a hydrogenation product of an aromatic carboxylic acid such that the aromatic carboxylic acid is dissolved in the solvent by recycling a portion of the reaction liquid. For hydrogenation of TPA to CHDA, the process claimed in this patent is not very useful for the following two reasons. First, no discovery is made in this patent as to the relationship between the relative use of solvent and product recirculation, and as a result, the total solvent flows required (as described in the examples) are still high and would lead to high initial costs and high energy costs for separation. Second, CHDA produced in accordance to this process will contain only 20 to 35% of the desirable trans isomer, and as a result, would require a separate and additional isomerization process (this is explained below) to enrich the trans content.

Based on this discussion, it is clearly evident that viable and practical process options do not exist for continuous production of CHDM and CHDA directly from TPA. Further developments and improved processes are needed, specifically to improve the solvent usage and therefore reduce the associated initial investment and energy usage while producing products rich in the desired trans isomers.

As mentioned earlier, isomeric compositions of CHDM and CHDA are important in polymer applications. High trans content is required to achieve many of the desirable end-use properties. For both CHDM and CHDA, isomerization requires bond-breaking and cannot be achieved simply through bond rotation. CHDA exhibits Lewis-acid catalyzed isomerization that proceeds through the enol formation mechanism. In the melt (above the melting point of trans CHDA), the mechanism is self-catalyzed and will lead to an equilibrium mixture containing ~66% trans CHDA. This however does not happen in the aqueous phase. For CHDM, isomerization is more complicated due to the —$CH_2OH$ side-chains. Metal alkoxide or hydroxide catalysts and severe reaction conditions are required and the yields are often poor.

Isomerization processes are known in the prior art. U.S. Pat. No. 2,917,549 (assigned to Eastman Kodak Company) discloses a process in which cis-CHDM is isomerized to trans-CHDM at temperatures in excess of 200° C. over metal alkoxide catalysts. U.S. Pat. No. 4,999,090 (assigned to Towa Chemical Industry Co., Ltd.) describes a process for isomerization of cis-CHDM to trans-CHDM in presence of alkali metal hydroxide or alkoxide catalysts. U.S. Pat. No. 7,595,423 (assigned to Mitsubishi Chemical Corporation) describes a process for isomerization of cis-CHDA to trans-CHDA that takes advantage of the melt-phase reaction mechanism described above. However, such isomerization processes essentially need to be carried out after separation of CHDA and CHDM as a product. Therefore they represent additional processing steps which lead to higher initial investment and higher operating costs, in addition to their inherent problems and difficulties. It is therefore beneficial to avoid the use and the need for such processes by obtaining product with desired cis/trans composition from the hydrogenation itself.

Industrial polymer applications require 65 to 70% trans content. The prior art processes for producing CHDM referenced earlier are capable of producing CHDM product with this trans content. However, the prior art processes for producing CHDA give CHDA with trans content of only about 20 to 35%. It will be greatly beneficial and highly desirable to obtain CHDA with higher trans content without the need for additional isomerization steps.

We should also note that presence of both cis and trans isomers in the hydrogenation products restricts the methods that can be used for product separation such that all of the cis and trans products need to be separated. Only a part of cis or a part of trans cannot be removed without the need for isomerization as it would mean accumulation of the other isomer in the process. For example, the use of crystallization and solid-liquid separation to separate only the trans product is not possible if we recycle the mother liquor rich in the cis isomer back to the process.

Based on this discussion on isomerization, it is clearly evident that any process for manufacture of CHDM should produce CHDM with trans content of at least 65-70% and any process for manufacture of CHDA should produce CHDA with trans content as high as possible.

Thus, further developments are needed.

SUMMARY OF THE INVENTION

Accordingly, embodiments of this invention provide greatly improved processes for continuous production of CHDM and CHDA by direct hydrogenation of TPA while promoting efficient use of solvent and energy and providing products with the desired high trans isomer content.

We have thoroughly investigated the solid-liquid equilibrium (hereinafter referred to as SLE) phase behavior of the TPA-CHDA system using water as the solvent. Based on this investigation of the SLE phase behavior, we have observed that complete dissolution of TPA prior to any reaction can be achieved using combination of solvent and recirculated CHDA solution. Furthermore, we have discovered that the SLE phase behavior is such that the flow requirements of solvent and product recirculation trend in the same direction—meaning that when solvent flow is reduced, the recirculation flow also decreases and vice-a-versa. Furthermore and unexpectedly, we have discovered that the recirculation flow requirement decreases increasingly rapidly with decreasing solvent flow with water as the solvent.

Based on these important discoveries, one embodiment of our invention is a process for continuous production of CHDM by direct hydrogenation of TPA that requires very small amounts of solvent for TPA dissolution, very reasonable amount of energy for product separation, and produces CHDM product with 65-70% trans content. In some embodiments, the process comprises the following steps:
1. Preparing a solution of TPA feed using recycled solvent (Step 5) and CHDA product solution recirculation (Step 3) using the dissolution chart, prepared based on the SLE phase behavior as a part of the method of this invention, such that TPA is completely dissolved at the desired reaction temperature;
2. Contacting the TPA solution with hydrogen in the first hydrogenation stage in presence of suitable catalyst in GLS reactors at temperature and pressure conditions such that TPA is substantially completely converted into CHDA via hydrogenation of the aromatic ring;
3. Recirculating a part of the CHDA product solution from the first hydrogenation stage back to preparation of TPA solution (Step 1);
4. Contacting the remaining CHDA product solution from the first hydrogenation stage with hydrogen in the second hydrogenation stage in presence of suitable catalyst in GLS reactors at temperature and pressure conditions such that the CHDA is substantially completely converted into CHDM via hydrogenation of the —COOH side-chains to —CH$_2$OH side-chains; and
5. Separating the CHDM product from the solvent by distillation and recycling a part of the solvent back to preparation of TPA solution (Step 1);

In the process described in the above embodiment, TPA is hydrogenated in two reaction stages. The aromatic ring is hydrogenated in the first stage and the —COOH side-chains are hydrogenated in the second stage. We have discovered that it is essential to preserve this sequence of stages as it would otherwise lead to severe by-product formation.

It is known that the dominant mechanism of reduction of —COOH groups of CHDA to —CH$_2$OH groups of CHDM is such that the cis/trans nature of the CHDA feed has little or no bearing on the cis/trans nature of the CHDM product. The cis/trans nature of the CHDM product is set mainly by the operating conditions, viz. temperature, pressure, and catalyst loading. In another embodiment of our invention, we have discovered that we can take advantage of this important behavior to create a process for simultaneous continuous production of CHDA and CHDM by direct hydrogenation of TPA. In another embodiments, the process comprises the following steps:

1. Preparing a solution of TPA feed using recycled solvent (Step 6) and CHDA product solution recirculation (Step 3) using the dissolution chart, prepared based on the SLE phase behavior as a part of the method of this invention, such that TPA is completely dissolved at the desired reaction temperature;
2. Contacting the TPA solution with hydrogen in the first hydrogenation stage in presence of suitable catalyst in GLS reactors at temperature and pressure conditions such that the TPA is substantially completely converted into CHDA via hydrogenation of the aromatic ring;
3. Recirculating a part of the CHDA product solution from the first hydrogenation stage back to preparation of TPA solution (Step 1);
4. Separating trans CHDA, by crystallization and subsequent solid-liquid separation, from the remaining part of the CHDA product solution from the first hydrogenation stage;
5. Contacting the cis CHDA rich mother liquor from the crystallization and subsequent solid-liquid separation with hydrogen in the second hydrogenation stage in presence of suitable catalyst in GLS reactors at temperature and pressure conditions such that the CHDA is substantially completely converted into CHDM via hydrogenation of the —COOH side-chains to —CH$_2$OH side chains; and
6. Separating the CHDM product from the solvent by distillation and recycling a part of the solvent back to preparation of TPA solution (Step 1);

This process takes advantage of the above noted peculiar feature of the reaction mechanism by using crystallization to separate trans CHDA and sending the remaining cis CHDA rich solution to the second stage and still get the CHDM product with desired trans content. This results in simultaneous production of 100% trans CHDA and 65-70% trans CHDM via one single process, without the need for any additional isomerization processes, and while still maintaining the solvent and energy efficiencies.

BRIEF DESCRIPTION OF THE FIGURES

All aspects, embodiments, and advantages of the invention will become apparent upon reading of the detailed description of the invention and the appended claims provided below, and upon reference to the drawings in which:

FIG. 6 shows a table highlighting the preferred operating conditions in terms of temperature, solvent flow, and product recirculation flow, thereby highlighting the advantages of this invention;

DETAILED DESCRIPTION OF THE INVENTION

Figure 1:
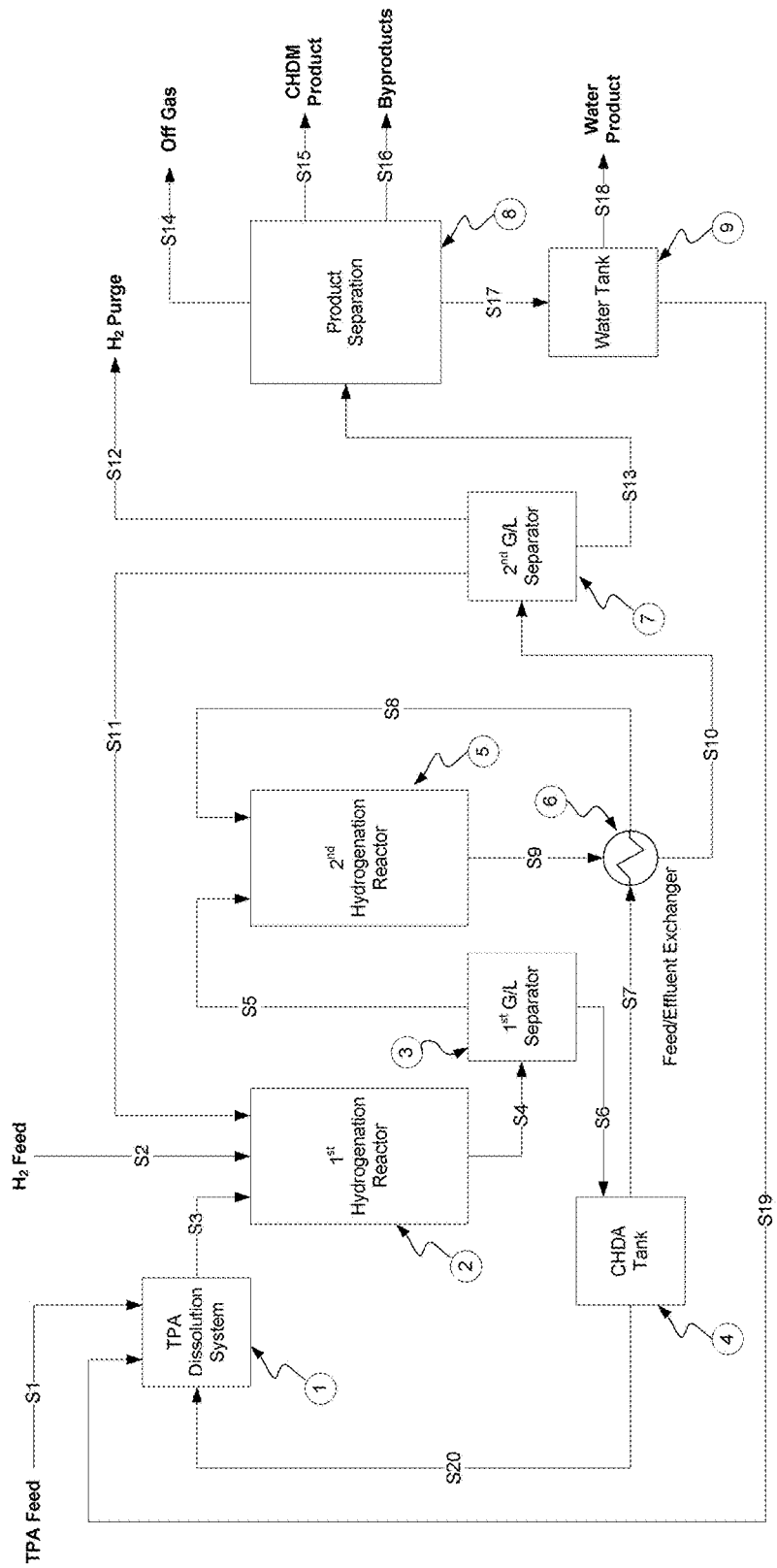
FIG. 1 shows a schematic flow diagram of a process for production of CHDM by direct hydrogenation of TPA according to one embodiment of this invention.

This invention provides greatly improved processes for production of CHDM and CHDA by direct hydrogenation of TPA while promoting efficient use of solvent and energy and providing products with the desired high trans isomer content. Accordingly, one embodiment of our invention is a process for production of CHDM by direct hydrogenation, comprising the following steps:
1. Preparing a solution of TPA feed using recycled solvent (Step 5) and CHDA product solution recirculation (Step 3) using the dissolution chart prepared based on the SLE phase behavior such that TPA is completely dissolved at the desired reaction temperature;
2. Contacting the TPA solution with hydrogen in the first hydrogenation stage in presence of suitable catalyst in GLS reactors at temperature and pressure conditions such that the TPA is substantially completely converted into CHDA via hydrogenation of the aromatic ring;
3. Recirculating a part of the CHDA product solution from the first hydrogenation stage back to preparation of TPA solution (Step 1);
4. Contacting the remaining CHDA product solution from the first hydrogenation stage with hydrogen in the second hydrogenation stage in presence of suitable catalyst in GLS reactors at temperature and pressure conditions such that the CHDA is substantially completely converted into CHDM via hydrogenation of the —COOH side-chains to —CH$_2$OH side chains;
5. Separating the CHDM product from the solvent by distillation and recycling a part of the solvent back to preparation of TPA solution (Step 1);

The system of this process, with water used as the solvent, is illustrated schematically in FIG. 1. In general, the system comprises TPA dissolution system 1, first hydrogenation reactor 2, first gas-liquid separator 3, CHDA tank 4, second hydrogenation reactor 5, feed-effluent exchanger 6, second gas-liquid separator 7, product separation system 8, and water tank 9. Solid TPA in powder form S1 is combined with recycled water S19 and aqueous CHDA product recirculation S20 in the TPA dissolution system 1. The resulting aqueous solution of TPA and CHDA S3, with TPA completely dissolved, is fed to the first hydrogenation reactor 2 along with fresh hydrogen feed S2 and recycled hydrogen S11, where it is contacted with suitable hydrogenation catalyst under suitable operating conditions such that TPA is substantially completely converted to CHDA and some byproducts. The effluent stream S4 is sent to the first gas-liquid separator 3. The separated gas stream S5 is sent to the second hydrogenation reactor 5 and the liquid stream, which is mainly an aqueous solution of CHDA, is sent to CHDA tank 4. A part of this aqueous CHDA solution is recirculated S20 to the TPA dissolution system 1, and the remainder is sent to the second hydrogenation reactor 5 via a feed-effluent heat exchanger 6. In the second hydrogenation reactor 5, the hot aqueous CHDA solution S8 and hydrogen S5 are contacted with suitable hydrogenation catalyst under suitable operating conditions such that CHDA is almost completely hydrogenated to CHDM and some byproducts. The heat of this hydrogenation reaction is removed by cooling the hot effluent stream S9 in the feed-effluent heat exchanger 6. The cooled effluent stream S10 is sent to the second gas-liquid separator 7, where some of the recovered gas is purged S12, most of the recovered gas is recycled S11 and the liquid stream S13, which is mainly an aqueous solution of CHDM is sent to the product separation system 8. Water S17 and CHDM product S18 are separated with very high purity specifications along with excess off-gas S14 and the byproducts S16. The separated water S17 is sent to the water tank 9. Water from this tank is recycled back S19 to the TPA dissolution system 1. The remaining water S18, which mainly is the water produced in the second hydrogenation reactor 5, is withdrawn as product.

Solid TPA in powder form and hydrogen gas are the starting raw materials for this process. Homogeneous solution containing the TPA feed needs to be created in the TPA dissolution system prior to the reaction stages. The key to creating such homogeneous solutions while using reasonably low amounts of total solvent are our discoveries, based on the SLE phase behavior, that solvent and product recirculation flows trend in the same direction and that the decrease in product recirculation becomes increasingly rapid with decrease in solvent flow especially when water is used as the solvent.

Figure 2:
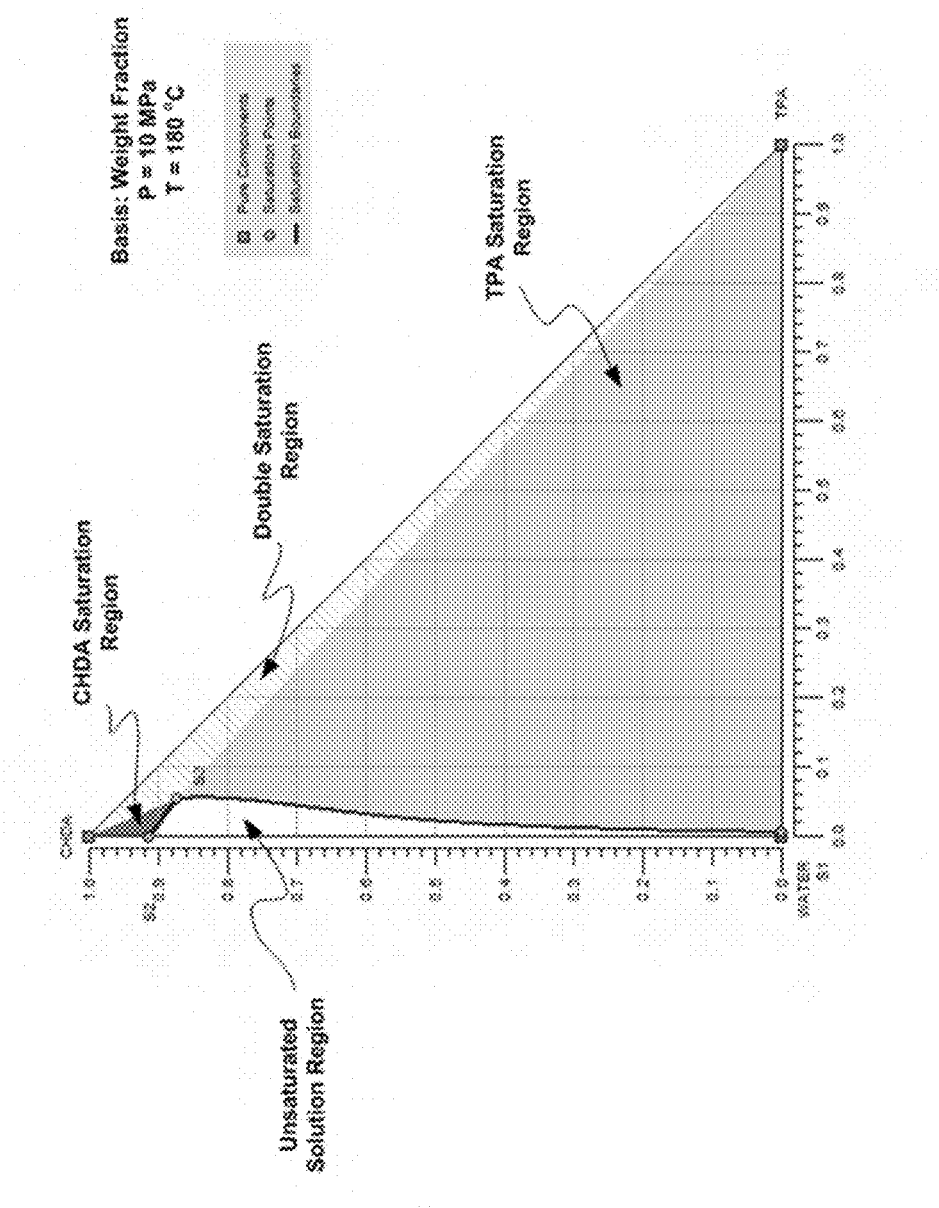
FIG. 2 shows the isothermal SLE phase behavior of the TPA-CHDA system with water as the solvent explaining the various features of the phase behavior.

These discoveries are based on and can be best explained using the SLE phase behavior of the TPA-CHDA system. FIG. 2 shows the SLE phase diagram at 10 MPa and 180° C., which are the preferred operating conditions for the first hydrogenation reactor, created based on our extensive investigation of the phase behavior with water as the solvent. This diagram is plotted as a triangle, with water, TPA and CHDA as the vertices and any mixture of the three components plotted within the triangular grid (X-axis being weight fraction of TPA and Y-axis being weight fraction of CHDA). Note that CHDA as represented on the phase diagram is a mixture of 75% cis and 25% trans isomers, which is the isomeric composition we expect from the first hydrogenation reactor. Key features of interest for us, as marked on the phase diagram, are as follows:
  The lightly-shaded region S1-S3-TPA represents the TPA saturation region. Any mixture with composition in this region will exist as a slurry containing undissolved TPA.
  The dark-shaded region S2-S3-CHDA represents the CHDA saturation region. Any mixture with composition in this region will exist as a slurry containing undissolved CHDA.
  The pattern-shaded region S3-CHDA-TPA represents the TPA-CHDA double saturation region. Any mixture with composition in this region will be a slurry containing both undissolved TPA and CHDA.
  The unshaded region W-S2-S3-S1 represents the unsaturation region. Any mixture with composition in this region will be in liquid phase, with both TPA and CHDA completely dissolved.
  S1-S3 represents the TPA saturation boundary and S2-S3 represents the CHDA saturation boundary. Saturation boundaries represent the solubility limits or the maximum amounts of the solutes that can be accommodated in solution.

Figure 3:
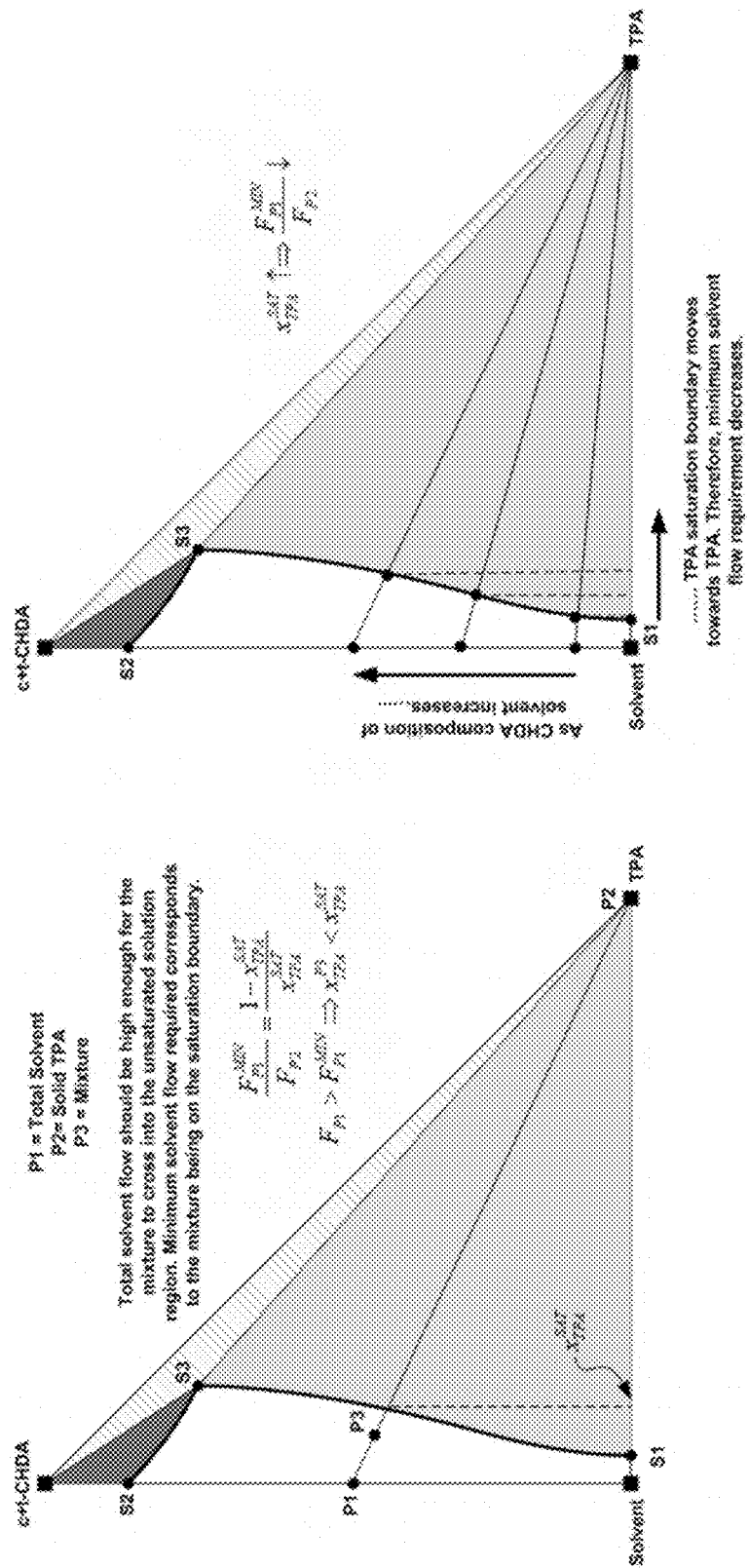
FIG. 3 shows a schematic representation of the SLE phase behavior explaining the discoveries made regarding the solvent and product recirculation flow requirements for complete dissolution of TPA.

Clearly, to achieve complete dissolution of TPA prior to reaction, we have to manipulate the combined composition of solvent, product recirculation, and solid TPA feed, such that it falls in the unsaturation region W-S2-S3-S1. This means that we have to have enough solvent to cross the TPA saturation boundary as explained in FIG. 3. This figure uses a schematic representation of the phase diagram of FIG. 2 for ease and clarity of presentation. As explained in FIG. 3, the minimum solvent flow (relative to solid TPA flow) for complete dissolution of TPA is that needed to cross the TPA saturation boundary. As the CHDA content of the solvent increases, the TPA saturation boundary moves to the right (towards TPA). This signifies increased solubility of TPA and decrease in solvent flow required for complete dissolution. This movement of the saturation boundary and the corresponding decrease in solvent flow required becomes more and more pronounced as the CHDA content of the solvent increases, especially when water is the solvent.

CHDA content of the product from the first hydrogenation reactor is set only by the relative flows of the solvent and solid TPA to the TPA dissolution system. This is easy to see from FIG. 1—we expect substantially complete conversion of TPA to CHDA in this reactor and the recirculation to TPA dissolution system is the same as the reactor product. Now, lower solvent flow means higher CHDA content in the reactor product and in the product recirculation. This in turn means higher CHDA content in the solvent used for TPA dissolution and therefore lower solvent flow as noted above. Similarly, higher solvent flow means lower CHDA content in the reactor product and in the product recirculation. This in turn means lower CHDA content in the solvent used for TPA dissolution and therefore higher solvent flow as noted above. Therefore, the solvent and product recirculation flows required to achieve complete TPA dissolution trend in the same direction. Also, the decrease in recirculation flow requirement becomes more rapid with decrease in solvent flow, especially with water as the solvent. This is due to the more and more pronounced movement of the TPA saturation boundary as noted on FIGS. 2 and 3.

SLE phase behavior in general, and in particular to this TPA-CHDA system, is not sensitive to pressure. Extensive investigation of SLE at temperatures from 150° C. to 200° C. (the preferable operating temperature range for the first hydrogenation reactor) reveals the same features of phase behavior noted above and therefore the same discoveries apply.

For ease of use as a part of the method of this invention, we have expressed these discoveries in mathematical form as follows:

$$\frac{F_{REC}^{MIN}}{F_{TPA}} + \frac{F_{SOLVENT}}{F_{TPA}} = \frac{1 - x_{TPA}^{SAT}}{x_{TPA}^{SAT}}$$

$$x_{TPA}^{SAT} = f(T, x)$$

Figure 4:
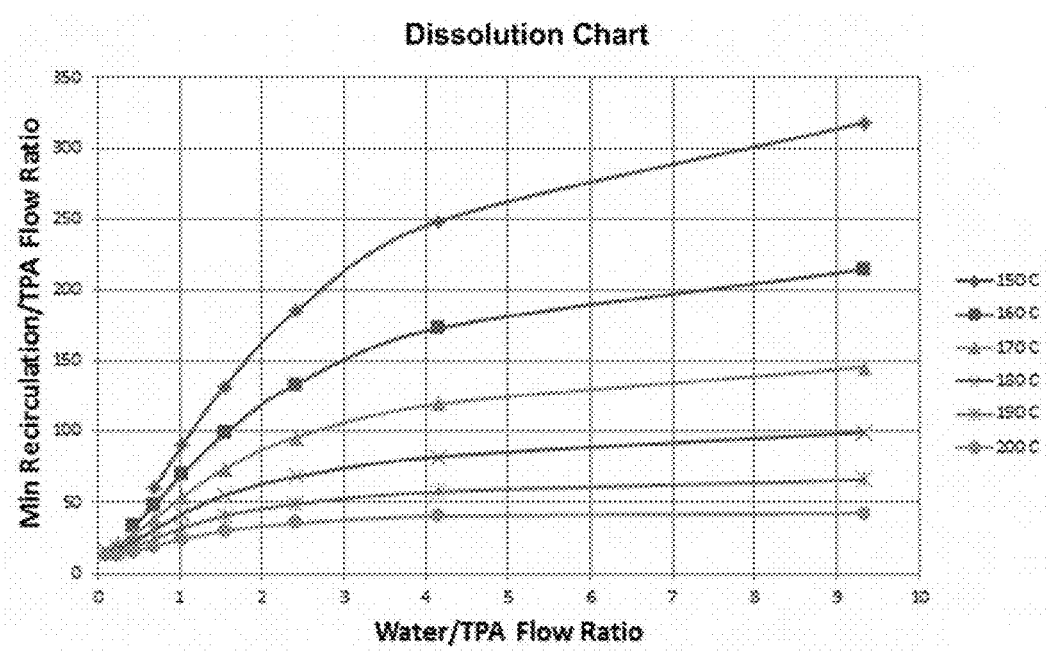
FIG. 4 shows a dissolution chart prepared based on the SLE phase behavior of the TPA-CHDA system with water as the solvent and as a part of the method of this invention.

Here, $F_{REC}^{MIN}$ is the minimum product recirculation flow required for complete dissolution of TPA, $F_{SOLVENT}$ is the flow of solvent used, $F_{TPA}$ is the flow of solid TPA raw material, and $x_{TPA}^{SAT}$ is the saturation weight fraction or the solubility limit of TPA which is a function of temperature and overall liquid composition. Now, by determining the TPA solubility limits (e.g. saturation boundary S1-S3 shown in FIGS. 2 & 3), through our extensive study of SLE phase behavior, we have created a chart correlating the minimum product recirculation flow to the flow of water. This chart, referred to as the dissolution chart, is shown in FIG. 4 for water as the solvent and provides a straightforward way of determining the minimum product recirculation flow required for a given solvent flow. Our discoveries can also be seen clearly from this chart. As the solvent (water) flow decreases, the minimum recirculation flow requirement also decreases for all temperatures of interest. The rate of decrease of the minimum recirculation flow requirement also becomes more rapid as the solvent (water) flow decreases.

Figure 5:
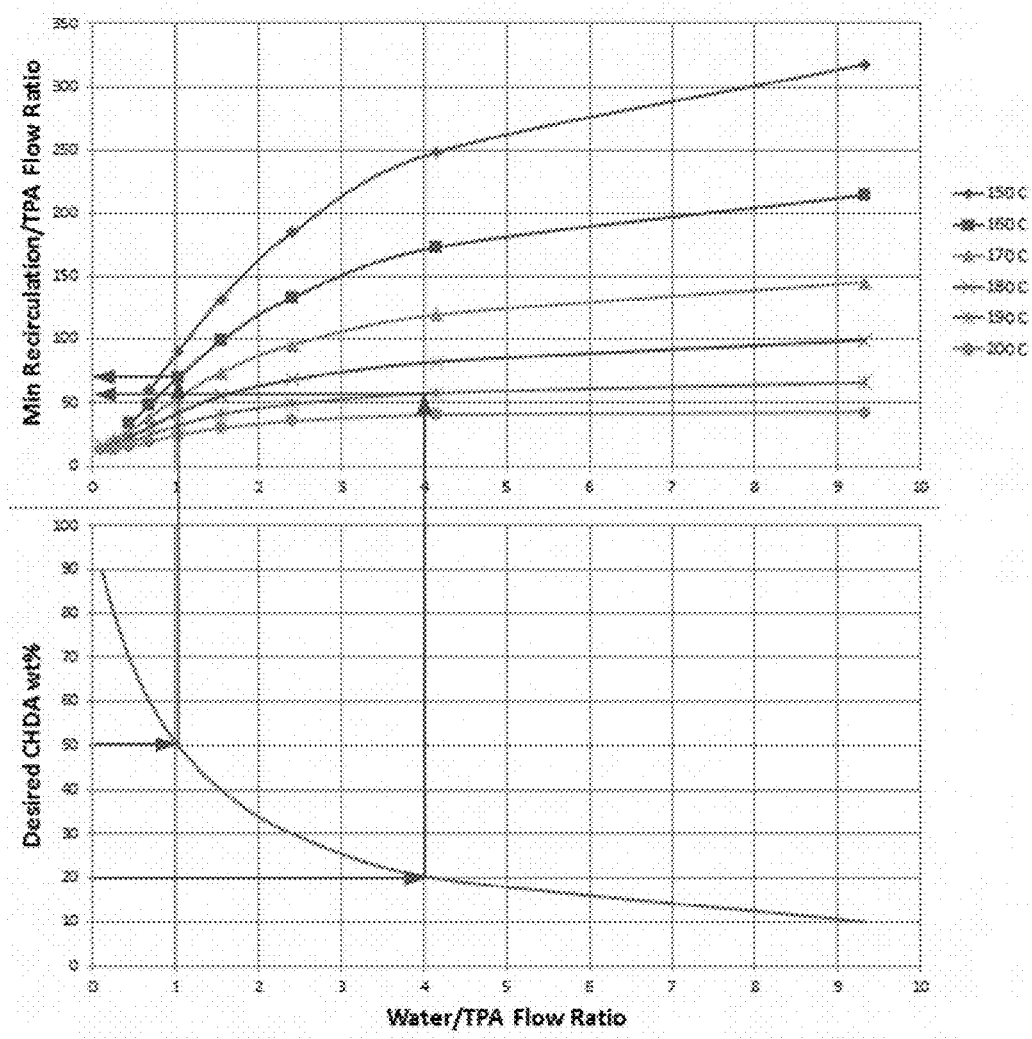
FIG. 5 illustrates the method based on the dissolution chart to determine the solvent and product recirculation flows for complete dissolution of TPA prior to reaction.

As discussed above, the CHDA content of the product from the first hydrogenation reactor is set only by the relative flows of the solvent and solid TPA feed. Combining this observation with the dissolution chart, we have created a step-by-step method to determine the solvent and product recirculation flows required for complete dissolution of TPA. The steps involved are listed below and are illustrated in FIG. 5 with water as the solvent:

1. Set the desired CHDA composition of the first hydrogenation reactor product
2. Using the chart at the bottom of FIG. 5, determine the solvent (water) flow required for the desired CHDA composition of the first hydrogenation reactor product
3. Using the dissolution chart at the top of FIG. 5, and using the above solvent (water) flow requirement, determine the minimum product recirculation required for complete dissolution of TPA at the desired reaction temperature
4. Set the actual product recirculation flow in excess of the minimum required High CHDA compositions favor less solvent and product recirculation flows. However, very high CHDA compositions are detrimental to catalyst life. Therefore, in Step 1 above, desired CHDA compositions should be in the range of 20 wt % to 50 wt %, preferably in the range of 30 wt % to 40 wt %. The preferences should be adjusted based on temperature for the first hydrogenation reactor. CHDA compositions at the higher end of this range should be used for lower temperatures and at the lower end of this range should be used for higher temperatures. Actual product recirculation flows should be in excess of the minimum required as listed in Step 4. The actual flows should be 5% to 20% in excess of minimum, most preferably 10% in excess of minimum.

FIG. 6 shows a table constructed using the above method with water as the solvent and considering product recirculation flows to be 10% in excess of minimum. The preferred operating conditions are highlighted in increasing shades of gray—the most preferred being the darkest shade. As can be seen clearly, complete dissolution of TPA can be achieved while using water flows only 1 to 2.5 times TPA by weight unlike the several hundred times that would be required by processes from prior art. Since this water has to be separated by distillation, this represents a significant reduction in energy used for separation. The product recirculation flows required are 35 to 75 times TPA by weight. Lower flows are required for lower water flows. Therefore, the total solvent flows are quite reasonable and much lower than the processes from prior art, thereby reducing the reactor and other equipment sizes.

The catalyst and operating conditions for the first hydrogenation reactor are chosen in order to achieve substantially complete conversion of TPA to CHDA by hydrogenation of the aromatic ring while keeping the formation of byproducts by decarboxylation, by decarbonylation, and by reduction of —COOH side-chains to —CH$_3$ side-chains to a minimum. Accordingly, palladium on activated carbon is used as the hydrogenation catalyst. Lower catalyst metal loadings provide longer catalyst life and lower byproduct formation through decarbonylation and reduction of —COOH side-chains to —CH$_3$ side-chains. However, they also lead to bigger reactors and higher cis content of the CHDA product.

Therefore, palladium loading of 0.1% to 5.0%, preferably 0.5% to 1.0% is used. Higher reaction temperatures lead to faster reactions and lower solvent and product recirculation flow rates; but lead to higher byproduct formation, especially by decarboxylation at temperatures in excess of 200° C. Therefore, the reactor may be operated at inlet temperatures from 150° C. to 200° C., preferably from 170° C. to 190° C. Higher reaction pressures lead to faster reactions and lower byproduct formation as decarbonylation and reduction of —COOH side-chains to —CH$_3$ become less significant. However, cis content of the CHDA produced as well as the operating costs increase with increasing pressure. Therefore, the reactor may be operated at pressures from 6 MPa to 12 MPa, preferably from 8 MPa to 10 MPa.

The most benefit can be derived by using the above operating conditions in a co-current down-flow trickle-bed GLS reactor. However, it will be easily apparent to those skilled in the art that other types of GLS reactors with different flow and hydrodynamic patterns can also be used. A single reactor operated as above is sufficient for obtaining the desired outcome from the hydrogenation reaction. However, those skilled in the art will realize that multiple reactors, either in series or in parallel, can be equivalently used to achieve the same results. The hydrogenation of aromatic ring is exothermic. The reactor is preferably operated adiabatically with the temperature allowed to increase along the reactor. This temperature rise is inherently limited due to the use of product recirculation as described earlier. The reactor product, under the preferred operating conditions, contains 75% cis CHDA and 25% trans CHDA.

The catalyst and operating conditions for the second hydrogenation reactor are also chosen in order to achieve substantially complete conversion of —COOH side-chains of CHDA to —CH$_2$OH side-chains in order to get CHDM while keeping byproduct formation to a minimum and ensuring the desired trans content for the CHDM product. Byproducts are formed by decarbonylation and by reduction of —COOH side-chains to —CH$_3$ side-chains, similar to the first hydrogenation. In addition, and to a lower extent, high-boiling ester oligomers are formed through reactions between —COOH and —CH$_2$OH side-chains. Hydrogenation of —COOH side-chains of CHDA to —CH$_2$OH side-chains requires activation of the C=O bonds. Accordingly, tin and ruthenium on activated carbon support is used as the hydrogenation catalyst. The tin is thought to initiate the hydrogenation by activating the C=O bonds and the ruthenium is thought to provide sites for hydrogen as well as for completing the hydrogenation. Higher metal loadings are desirable because lower loadings lead to lower trans content of the CHDM product. However, very high loadings cause metal elution due to the acidic nature of the reaction contents. Also, higher tin to ruthenium ratio leads to faster reactions but favors cis CHDM formation. Therefore, metal loadings of 1% to 10% with tin to ruthenium ratio of 1:1 to 1:2, preferably 5% tin and 7% ruthenium are used.

Higher reaction temperatures lead to increased byproduct formation, especially at temperatures greater than 270° C. However, high temperatures strongly favor formation of trans CHDM over cis CHDM and also offer higher reaction rates. Therefore, the reactor may be operated at inlet temperatures of 220° C. to 250° C., preferably from 230° C. to 240° C. Higher pressures lead to faster reactions but favor formation of cis CHDM. Therefore, operation at lower pressures is preferred. However, the lower pressure levels are limited by the necessity of maintaining the solution in liquid phase at the high reaction temperatures. Therefore, the reactor may be operated at pressures from 6 MPa to 12 MPa, preferably from 8 MPa to 10 MPa. It is preferred that the operating pressure of this second hydrogenation stage be lower than the first hydrogenation stage so that the hydrogen from the first stage can be used directly for the second stage without the need for re-compression.

Here also, the most benefit can be derived by using the above operating conditions in a co-current down-flow trickle-bed GLS reactor. However, it will be easily apparent to those skilled in the art that other types of GLS reactors with different flow and hydrodynamic patterns can also be used. A single reactor operated as above is sufficient for obtaining the desired outcome from the hydrogenation reaction. However, it will also be apparent to persons skilled in the art that that multiple reactors, either in series or in parallel, can be equivalently used to achieve the same results. This hydrogenation is also exothermic. It is still preferred that the reactor be operated adiabatically because higher temperatures promote trans-CHDM formation. However, to minimize byproduct formation, it is desirable to limit the temperature increase along the reactor to 10° C. to 40° C., depending on the chosen temperature at the reactor inlet. If necessary, and although not shown in FIG. 1, recirculation of cooled liquid product should be used for this second hydrogenation reactor in order to limit the temperature rise along the reactor.

The effluent stream from the second gas-liquid separator mainly contains CHDM product, solvent, water produced in the second hydrogenation reactor, and minor amounts of impurities. Water is a natural choice for solvent as it is produced in the second hydrogenation reactor. The CHDM product, under the preferred operating conditions, contains 25-35% cis CHDM and 65-75% trans CHDM. The purity specifications are very strict—final CHDM product needs to be >99.5% pure by weight and the solvent (and water) need to contain CHDM and other impurities in ppm amounts so that it can be recycled and used for other purposes. Also, the cis/trans content of the CHDM product needs to be preserved. Therefore, the separation is achieved by distillation. The low solvent flow used for TPA dissolution (only 1 to 2.5 times TPA feed flow by weight with water as the solvent) proves very advantageous in limiting the energy required for separation of solvent and CHDM by distillation.

Figure 7:
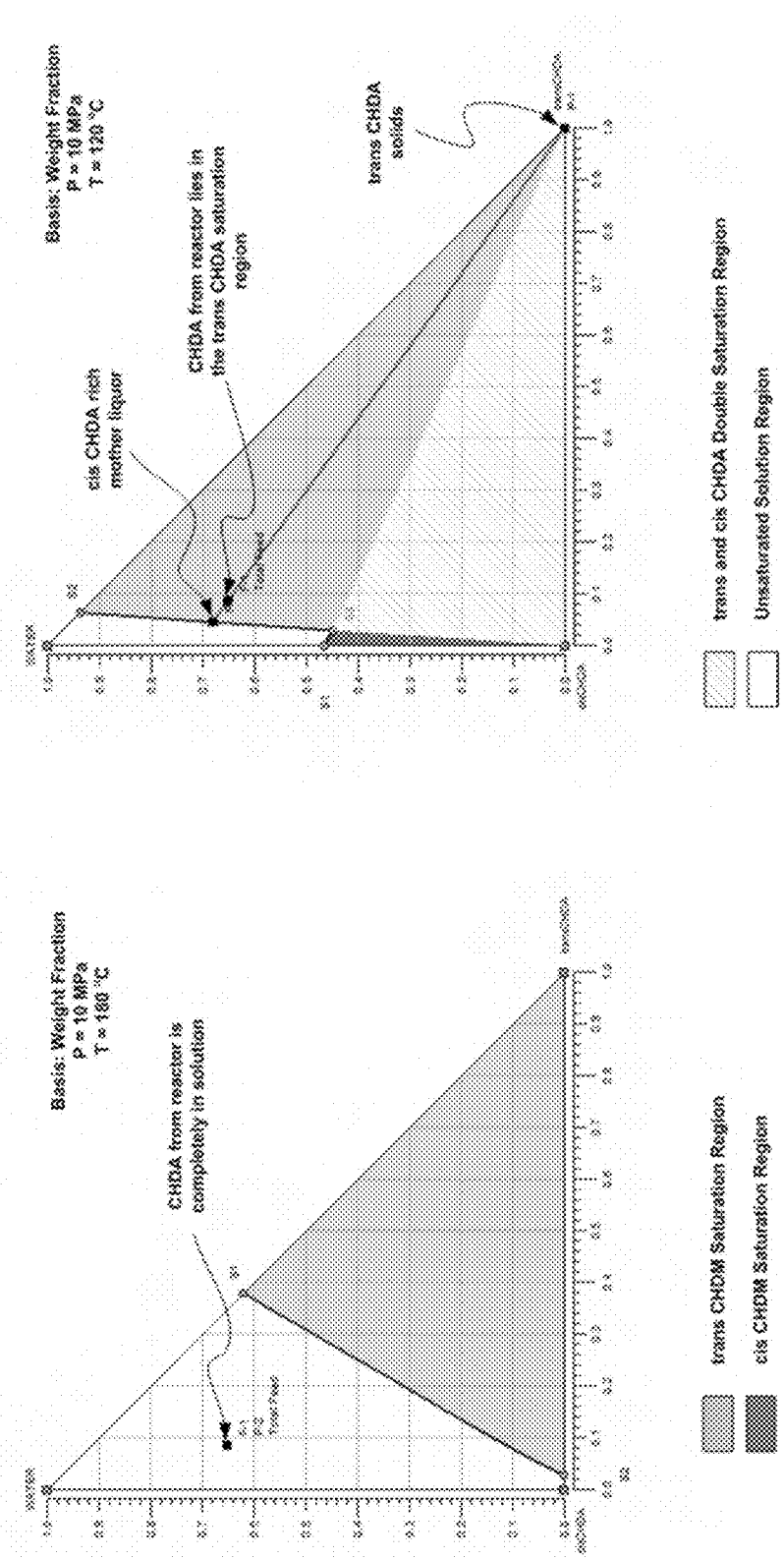
FIG. 7 shows isothermal phase behavior of the CHDA solution with water as the solvent explaining the basis for obtaining 100% trans CHDA as product from a crystallization based separation process.

Another important aspect of the SLE phase behavior is revealed by the CHDA solution system. FIG. 7 shows the isothermal SLE phase diagrams at 180° C. and 120° C., with water as the solvent. In principle, these phase diagrams are similar to those in FIGS. 2 and 3, the only difference being that TPA is not involved and the stereo-isomeric forms of CHDA are now plotted separately. In addition to the saturation regions and boundaries, FIG. 7 also shows the composition of the product stream from the first hydrogenation reactor operated under the preferred operating conditions (35 wt % CHDA, 25% cis). At 180° C., the product is homogeneous liquid as expected. However, at 120° C., the product now moves into the trans CHDA saturation region and would therefore crystallize to give trans CHDA solids and cis CHDA rich liquid.

Figure 8:
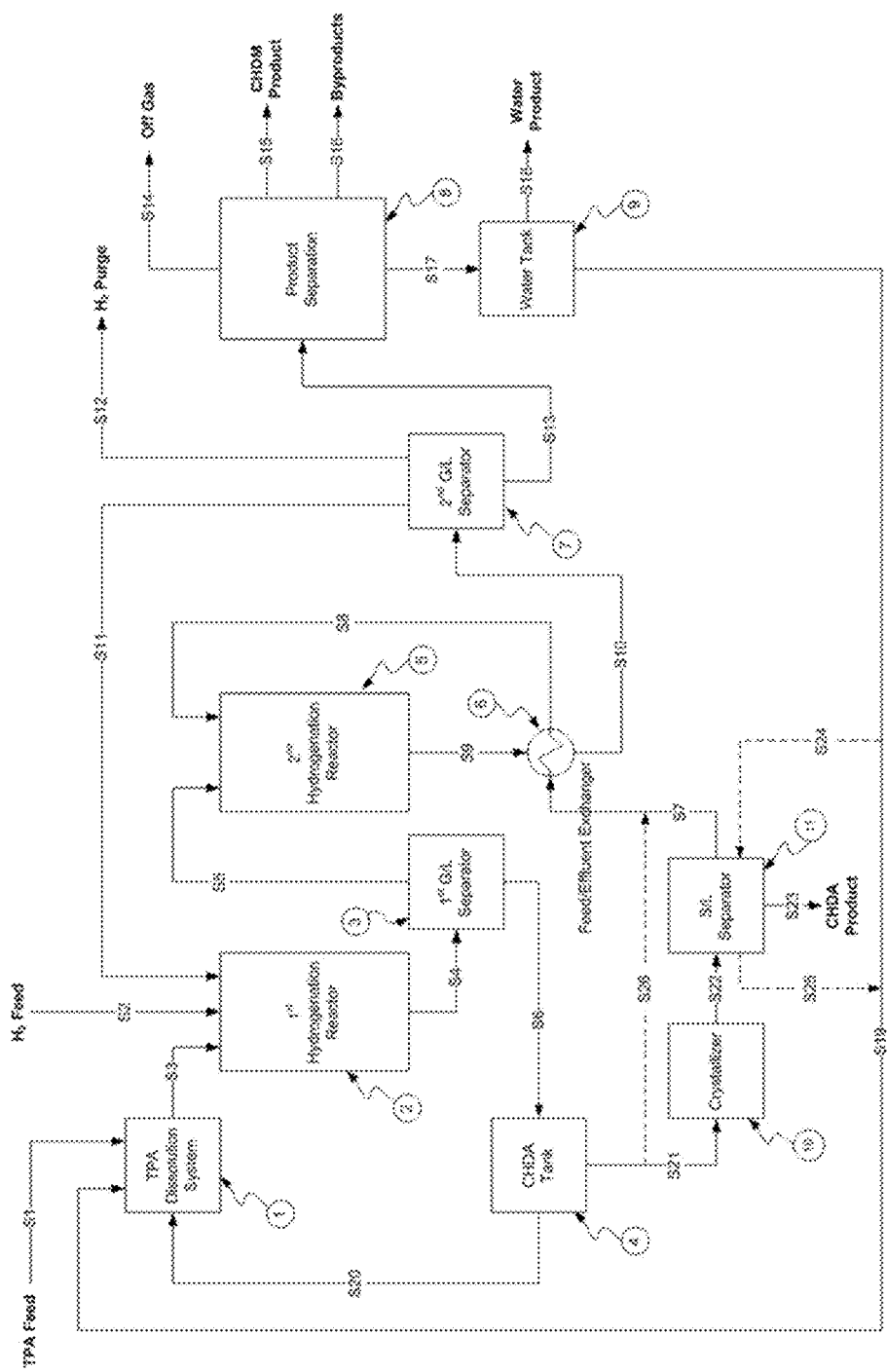
FIG. 8 shows a schematic flow diagram of a process for simultaneous production of CHDM and CHDA by direct hydrogenation of TPA according to another embodiment of this invention that uses crystallization to obtain 100% CHDA as an intermediate step.

Ordinarily, the above would not be much useful—because although we get 100% trans CHDA product, we are still left with a large quantity of cis CHDA rich liquid. Fortunately, the dominant mechanism of reduction of —COOH groups of CHDA to —CH$_2$OH groups of CHDM is such that the cis/trans nature of the CHDA feed has little or no bearing on the cis/trans nature of the CHDM product. The cis/trans nature of the CHDM product is set mainly by the operating conditions, viz. temperature, pressure, and catalyst loading of the second hydrogenation reactor. This therefore provides us a way to use the cis CHDA rich liquid for production of CHDM through the second hydrogenation reactor, without compromising the trans content of the CHDM produced in this reactor. Accordingly, another embodiment of our invention is a process for simultaneously producing 100% trans CHDA and 65-75% trans CHDM by direct hydrogenation of TPA, comprising the following steps:

1. Preparing a solution of TPA feed using recycled solvent (Step 6) and CHDA product solution recirculation (Step 3) using the dissolution chart prepared based on the SLE phase behavior such that TPA is completely dissolved at the desired reaction temperature;
2. Contacting the TPA solution with hydrogen in the first hydrogenation stage in presence of suitable catalyst in GLS reactors at temperature and pressure conditions such that the TPA is substantially completely converted into CHDA via hydrogenation of the aromatic ring;
3. Recirculating a part of the CHDA product solution from the first hydrogenation stage back to preparation of TPA solution (Step 1);
4. Separating trans CHDA, by crystallization and subsequent solid-liquid separation, from the remaining part of the CHDA product solution from the first hydrogenation stage;
5. Contacting the cis CHDA rich mother liquor from the crystallization and subsequent solid-liquid separation with hydrogen in the second hydrogenation stage in presence of suitable catalyst in GLS reactors at temperature and pressure conditions such that the dissolved CHDA is substantially completely converted into CHDM via hydrogenation of the —COOH side-chains to —CH$_2$OH side chains;
6. Separating the CHDM product from the solvent by distillation and recycling a part of the solvent back to preparation of TPA solution (Step 1);

The system of this process, with water used as the solvent, is illustrated schematically in FIG. 8. The system is similar to the system of FIG. 1, except for the crystallization 10 and solid-liquid separation 11 steps. Therefore, only these steps are described here. The part of the CHDA product stream S21 that is not used as product circulation is sent to a crystallizer 10. In the crystallizer, a part of the trans CHDA in the product stream separates as solids. The slurry from the crystallizer S22 is sent to the solid-liquid separation system 11 where 100% trans CHDA in solid phase is obtained as the product S23 and the remaining liquid (mother liquor) S7 that is now richer in cis CHDA is sent to the second hydrogenation reactor via the feed effluent heat exchanger.

The crystallizer should be operated in such a way that the overall composition lies in the trans CHDA saturation region at the temperature of operation. The cis and trans CHDA double saturation region should be avoided. Depending on the CHDA content of the first hydrogenation reactor product, the crystallization temperature should range from 100° C. to 150° C. and preferably from 120° C. to 140° C. The temperature reduction required for crystallization can be brought about by cooling by heat transfer or by adiabatic evaporative cooling or by combination of the two. Adiabatic evaporative cooling by lowering the pressure and causing solvent to evaporate is preferred as it not only leads to temperature reduction but also leads to concentration of CHDA content. Although only one crystallizer is shown in FIG. 8, those familiar with the art will realize that multiple crystallizers either in series or in parallel could equivalently be used. Solid-liquid separation operations involve filtration, washing, and drying of the trans CHDA product. If washing operation is used, part of the recycle solvent (water) stream should be used as the wash liquid as shown by the dotted streams S24 and S25 originating and culminating on stream S19 on FIG. 8.

It is necessary to operate the crystallizer in the trans CHDA saturation region in order to separate 100% trans CHDA as solids. As a result, when operated in this region, the trans content of the feed to the crystallizer puts a limit on CHDA production rates. If very high CHDA production rates are required, it is possible to operate in the cis and trans CHDA double saturation region. In such an operation, the solids product will not be 100% trans CHDA but will still have trans content much higher than that of the crystallizer feed. Also note that, it is not necessary to use the CHDA stream S21 in its entirety to separate trans CHDA by crystallization. Part of the CHDA stream could be sent directly to the second hydrogenation reactor, as shown by the dotted stream S26 on FIG. 8, while trans CHDA is recovered from the remaining part. Depending on the relative demands for CHDA and CHDM, and on other market driving forces, the flow rate of stream S26 could be manipulated to adjust the production rates.

All other aspects of this embodiment, including the first hydrogenation reactor, second hydrogenation reactor, and product separation system, should be operated as discussed previously. Based on the SLE phase behavior of the CHDA solution system, and by taking advantage of the peculiar features of the mechanism for hydrogenation of CHDA to CHDM, the process of this embodiment can produce 100% trans CHDA and 65% to 75% trans CHDM, unlike any other process in the prior art.

EXAMPLES

Examples are provided in this section to further highlight certain aspects and advantages of the system and method of this invention. These examples are provided for illustration purposes only and are not intended in any way of form to limit the scope of this invention.

Examples 1-3

These examples are provided to highlight and validate the use of the method based on the dissolution chart for setting solvent and recirculation flows. For each of these examples, a slurry was prepared in a stirred autoclave, by mixing pre-determined amounts of water, TPA in powder form, and CHDA (22% trans) in powder form. The autoclave was then pressurized to 10 MPa using nitrogen gas and the temperature was then raised to the pre-determined level. Samples were drawn after 15 minutes of operation at this temperature level and analyzed to determine the compositions of TPA and CHDA.

The predetermined feed mixture compositions and the pre-determined temperature levels for these experiments are shown in Table 1 below. Each pre-determined feed mixture composition is chosen such that it very closely corresponds to water/TPA and recirculation/TPA flow ratios that may be used in actual operation according to the preferred values from FIG. 6. These ratios are also listed in Table 1.

TABLE 1

|  |  | Example 1 | Example 2 | Example 3 |
|---|---|---|---|---|
| Operating | wt % TPA | 1.9 | 1.7 | 1.8 |
| Conditions | wt % CHDA | 28.1 | 38.3 | 48.2 |
|  | wt % Water | 70.0 | 60.0 | 50.0 |
|  | Temperature (° C.) | 190 | 180 | 170 |
| Flow Ratios | Water/TPA | 2.42 | 1.55 | 1.04 |
|  | Recirculation/TPA | 53.84 | 60.69 | 59.42 |

In each example, the TPA and CHDA compositions of the samples taken at the end of operation were found to be equivalent to the starting feed mixture compositions. This implies that TPA and CHDA are both completely dissolved in solution, as indicated by our use of the dissolution chart.

Example 4

This is a simulation example provided to highlight the process for production of CHDM from TPA. Reference is made to the system of FIG. 1 for the unit operations involved and for the stream numbers.

TABLE 2

| Stream ID | S1 | S19 | S20 |
|---|---|---|---|
| Description | TPA Feed | Water Recycle | Product Recirculation |
| Total Flow (kg/h) | 1000 | 1920 | 68076 |
| Composition (wt %) | | | |
| TPA | 100.000 | 0.000 | 0.014 |
| CHDA | 0.000 | 0.000 | 34.359 |
| CHDM | 0.000 | 0.002 | 0.000 |
| Water | 0.000 | 99.997 | 65.039 |
| Byproducts | 0.000 | 0.001 | 0.588 |

The TPA dissolution system is operated at 180° C. with water as the solvent. Using the dissolution chart and the method based on the dissolution chart as described in this invention, the water and product recirculation flows are set such that the CHDA product from the first hydrogenation reactor contains ~35% CHDA by weight and 10% excess recirculation flow is used for complete dissolution of TPA. The first hydrogenation reactor is operated at 180° C. inlet temperature and 10 MPa pressure. The second hydrogenation reactor is operated at 230° C. inlet temperature and 8 MPa pressure. Water, CHDM product, and by-products are separated using a four column distillation system with purity specifications of >99.5% by weight pure CHDM product and <50 ppm CHDM and other impurities in the water.

Total flow rates and compositions (weight percent) for the streams to the TPA dissolution system are shown in Table 2 and for other major streams are shown in Table 3. The flow rates are shown on the basis of TPA feed flow of 1000 kg/h.

TABLE 3

| Stream ID | S7 | S13 | S15 | S18 |
|---|---|---|---|---|
| Description | Feed to Second Reactor | Product from Second Reactor | CHDM Product | Water Product |
| Total Flow (kg/h) | 2955 | 2999 | 781 | 215 |
| Composition (wt %) | | | | |
| TPA | 0.014 | 0.000 | 0.000 | 0.000 |
| CHDA | 34.359 | 0.041 | 0.000 | 0.000 |
| CHDM | 0.000 | 27.036 | 99.993 | 0.002 |
| Water | 65.039 | 71.267 | 0.000 | 99.997 |
| Byproducts | 0.588 | 1.656 | 0.007 | 0.001 |

In the first hydrogenation reactor, 99% of TPA in the feed to the reactor is reacted with 98% selectivity to CHDA. In the second hydrogenation reactor, 99% of CHDA is hydrogenated but the effective selectivity to CHDM is only about 95%. TPA remaining in the feed to the second hydrogenation reactor is completely hydrogenated—but mainly to give byproducts due to the nature of the catalyst. The trans content of the CHDM product is 70%.

Water/TPA flow ratio of 1.92 and recirculation/TPA flow ratio of 68.08 is used to ensure complete dissolution of TPA prior to the first hydrogenation reactor. The product separation system has to separate the second hydrogenation reactor product stream containing roughly by weight 27% CHDM, 71% water, and rest unreacted reactants and impurities. The total reboiler duty required for recovering CHDM product and water according to the purity specifications is 6590 kJ/kg TPA feed.

Examples 5-8

These simulation examples are provided to highlight the energy savings benefit from using lower solvent and lower product recirculation flows for complete dissolution of TPA as per our invention. Reference is made to the system of FIG. 1 and water is used as the solvent. In Examples 5, 6, 7, and 8, the water and product recirculation flows required for complete dissolution of TPA are set based on the dissolution chart based method of this invention in such a way that the CHDA content of the first hydrogenation reaction product is roughly 20%, 30%, 40% and 50% by weight, respectively. In all other respects the process is operated in exactly the same way as described in Example 4.

Table 4 summarizes the flow requirements, resulting CHDA content of the first hydrogenation reactor product, and the energy required for separation of CHDM product and water. The energy savings from the ability to use lower water flows are clearly evident.

TABLE 4

| | Example 5 | Example 6 | Example 7 | Example 8 |
|---|---|---|---|---|
| Water/TPA Flow Ratio | 4.15 | 2.42 | 1.55 | 1.04 |
| Recirculation/TPA Flow Ratio | 90.84 | 75.07 | 60.77 | 46.75 |
| wt % CHDA | 19.58 | 29.39 | 39.28 | 48.93 |
| Separation Energy (kJ/kg TPA) | 12978 | 8064 | 5540 | 4131 |

Example 9

This simulation example is provided to highlight the process for simultaneous production of CHDA and CHDM from TPA. Reference is made to FIG. 8 the unit operations involved and for the stream numbers.

TABLE 5

| Stream ID | S1 | S19 | S20 | S23 |
|---|---|---|---|---|
| Description | TPA Feed | Water Recycle | Product Recirculation | trans CHDA Product |
| Total Flow (kg/h) | 1000 | 1040 | 46745 | 93 |
| Composition (wt %) | | | | |
| TPA | 100.000 | 0.000 | 0.021 | 0.000 |
| CHDA | 0.000 | 0.000 | 48.931 | 99.870 |
| CHDM | 0.000 | 0.004 | 0.000 | 0.000 |
| Water | 0.000 | 99.995 | 50.200 | 0.130 |
| Byproducts | 0.000 | 0.001 | 0.848 | 0.000 |

The TPA dissolution system and the hydrogenation reactor are operated at the conditions of Example 8 above. The only difference being the use of crystallization at 120° C. for separating trans CHDA from the feed to the second hydrogenation reactor. Total flow rates and compositions (weight percent) of major streams are shown in Tables 5 & 6. The flow rates are shown on the basis of TPA feed flow of 1000 kg/h.

TABLE 6

| Stream ID | S7 | S13 | S15 | S18 |
|---|---|---|---|---|
| Description | Feed to Second Reactor | Product from Second Reactor | CHDM Product | Water Product |
| Total Flow (kg/h) | 1982 | 2023 | 703 | 194 |
| Composition (wt %) | | | | |
| TPA | 0.022 | 0.000 | 0.000 | 0.000 |
| CHDA | 46.602 | 0.055 | 0.000 | 0.000 |
| CHDM | 0.000 | 36.491 | 99.998 | 0.004 |
| Water | 52.488 | 61.151 | 0.000 | 99.995 |
| Byproducts | 0.888 | 2.303 | 0.002 | 0.001 |

This process produces 0.093 kg 100% trans CHDA and 0.703 kg CHDM with 70% trans content per kg of TPA feed.

We claim:

1. A method for continuous production of CHDM by direct hydrogenation TPA, comprising the steps of:
    preparing a solution of TPA feed using recycled solvent and CHDA product solution recirculation such that TPA is completely dissolved at a desired reaction temperature;
    contacting the TPA solution with hydrogen in a first hydrogenation stage in presence of a suitable catalyst in one or more GLS reactors at temperature and pressure conditions such that the TPA is converted into CHDA via hydrogenation of the aromatic ring to produce the CHDA product solution;
    recirculating a part of the CHDA product solution from the first hydrogenation stage back to the step of preparation of the TPA solution;
    contacting the remaining CHDA product solution from the first hydrogenation stage with hydrogen in a second hydrogenation stage in presence of a suitable catalyst in one or more GLS reactors at temperature and pressure conditions such that the CHDA is converted into CHDM via hydrogenation of the —COOH side-chains to —CH$_2$OH side chains to produce a CHDM product; and
    separating the CHDM product from the solvent by distillation and recycling a part of the solvent back to the step of preparation of TPA solution.

2. The method according to claim 1, where the solvent is water.

3. The method according to claim 1, in which the first hydrogenation reaction is carried out in a GLS reactor with a fixed catalyst bed.

4. The method according to claim 3, wherein the fixed catalyst bed is a trickle bed reactor or an adiabatic co-current down-flow trickle bed reactor.

5. The method according to claim 1, in which the catalyst for the first hydrogenation reaction is a noble metal catalyst on porous support.

6. The method according to claim 1, in which the catalyst metal loading for the first hydrogenation reaction is 0.1% to 5%.

7. The method according to claim 1, in which the first hydrogenation reactor is operated such that the inlet temperatures are from 150° C. to 200° C.

8. The method according to claim 1, in which the first hydrogenation reactor is operated at pressures from 6 MPa to 12 MPa.

9. The method according to claim 1, in which the second hydrogenation reaction is carried out in a GLS reactor with a fixed catalyst bed.

10. The method according to claim 1, wherein the fixed catalyst bed is a trickle bed reactor or an adiabatic co-current down-flow trickle bed reactor.

11. The method according to claim 1, in which the catalyst for the second hydrogenation reaction is a bimetallic combination of noble metal and carbonyl bond activator on a porous support.

12. The method according to claim 1, in which the catalyst metal loading for the second hydrogenation reaction is 1% to 10% with tin to ruthenium ratio of 1:1 to 1:2.

13. The method according to claim 1, in which the second hydrogenation reactor is operated such that the inlet temperatures are from 220° C. to 250° C.

14. The method according to claim 1, in which the first hydrogenation reactor is operated at pressures from 6 MPa to 12 MPa.

15. The method according to claim 1, where the second hydrogenation reactor is operated at a pressure lower than the first hydrogenation reactor in such a way that the hydrogen is first fed to the first hydrogenation reactor and then sent to the second hydrogenation reactor without the need for recompression.

16. The method according to claim 1, in which the CHDA concentration in the first hydrogenation reactor product is maintained at 20% to 50% by weight.

17. The method according to claim 1, in which water used as solvent is only 1 to 4 times TPA feed by weight.

18. The method according to claim 1 wherein the method produces CHDM product with 65% to 75% trans content.

19. A method for continuous production of CHDA and CHDM by direct hydrogenation of TPA, comprising the steps of:
    preparing a solution of TPA feed using recycled solvent and CHDA product solution recirculation such that TPA is completely dissolved at a desired reaction temperature;
    contacting the TPA solution with hydrogen in a first hydrogenation stage in presence of suitable catalyst in one or more GLS reactors at temperature and pressure conditions such that the TPA is converted into CHDA via hydrogenation of the aromatic ring to produce the CHDA product solution;
    recirculating a part of the CHDA product solution from the first hydrogenation stage back to the step of preparation of the TPA solution;
    separating trans CHDA, by crystallization and subsequent solid-liquid separation, from the remaining part of the CHDA product solution from the first hydrogenation stage;
    contacting cis CHDA rich mother liquor from the crystallization and subsequent solid-liquid separation with hydrogen in a second hydrogenation stage in presence of suitable catalyst in GLS reactors at temperature and pressure conditions such that the CHDA is converted into CHDM via hydrogenation of the —COOH side-chains to —CH$_2$OH side chains to produce a CHDM product; and
    separating the CHDM product from the solvent by distillation and recycling a part of the solvent back to the step of preparation of TPA solution,
    wherein the trans CHDA or trans CHDA rich solids product is separated by crystallization from the product of the first hydrogenation reactor and the cis CHDA rich mother liquor is hydrogenated in the second hydrogenation reactor without affecting the trans content of the CHDM produced in the reactor.

20. The method according to claim 19, where the solvent is water.

21. The method according to claim 19, in which the first hydrogenation reaction is carried out in a GLS reactor with a fixed catalyst bed, selected from one of: a trickle bed reactor, or an adiabatic co-current down-flow trickle bed reactor.

22. The method according to claim 19, in which the catalyst for the first hydrogenation reaction is a noble metal catalyst on porous support.

23. The method according to claim 19, in which the catalyst metal loading for the first hydrogenation reaction is 0.1% to 5%.

24. The method according to claim 19, in which the first hydrogenation reactor is operated at inlet temperatures from 150° C. to 200° C.

25. The method according to claim 19, in which the first hydrogenation reactor is operated at pressures from 6 MPa to 12 MPa.

26. The method according to claim 19, in which the second hydrogenation reaction is carried out in a GLS reactor with a fixed catalyst bed, selected from one of: in a trickle bed reactor or an adiabatic co-current down-flow trickle bed reactor.

27. The method according to claim 19, in which the catalyst for the second hydrogenation reaction is a bimetallic combination of noble metal and carbonyl bond activator on a porous support.

28. The method according to claim 19, in which the catalyst metal loading for the second hydrogenation reaction is 1% to 10% with tin to ruthenium ratio of 1:1 to 1:2.

29. The method according to claim 19, in which the second hydrogenation reactor is operated at inlet temperatures from 220° C. to 250° C.

30. The method according to claim 19, where the second hydrogenation reactor is operated at a pressure lower than the first hydrogenation reactor so that the hydrogen is first fed to the first hydrogenation reactor and then sent to the second hydrogenation reactor without the need for recompression.

31. The method according to claim 19, in which the CHDA concentration in the first hydrogenation reactor product is maintained at 20% to 50% by weight.

32. The method according to claim 19, in which water used as solvent is only 1 to 4 times TPA feed by weight.

33. A system and method according to claim 19, where 100% trans CHDA is separated at by crystallization at temperatures from 100° C. to 150° C.

34. The method according to claim 19 wherein the process produces 100% trans CHDA and CHDM product with 65% to 75% trans content through a single process without the need for additional isomerization steps.

35. The method according to claim 19 wherein the production rates of CHDA and CHDM is adjusted by adjusting trans CHDA separation by crystallization.

36. The method according to claim 19, in which the catalyst for the first hydrogenation reaction is palladium on activated carbon support.

37. The method according to claim 19, in which the catalyst metal loading for the first hydrogenation reaction is 0.5% to 1%.

38. The method according to claim 19, in which the first hydrogenation reactor is operated at inlet temperatures from 170° C. to 190° C.

39. The method according to claim 19, in which the first hydrogenation reactor is operated at pressures from 8 MPa to 10 MPa.

40. The method according to claim 19, in which the catalyst for the second hydrogenation reaction is ruthenium and tin on activated carbon support.

41. The method according to claim 19, in which the catalyst metal loading for the second hydrogenation reaction is 1% to 10% with tin to ruthenium ratio of 5% tin and 7% ruthenium.

42. The method according to claim 19, in which the second hydrogenation reactor is operated at inlet temperatures from 230° C. to 240° C.

43. The method according to claim 19, in which the CHDA concentration in the first hydrogenation reactor product is maintained at 30% to 40% by weight.

44. The method according to claim 19, in which water used as solvent is only 1 to 2.5 times the TPA feed by weight.

45. A system and method according to claim 19, where 100% trans CHDA is separated at by crystallization at temperatures from 120° C. to 140° C.

46. The method according to claim 1, in which the catalyst for the first hydrogenation reaction is palladium on activated carbon support.

47. The method according to claim 1, in which the catalyst metal loading for the first hydrogenation reaction is 0.5% to 1%.

48. The method according to claim 1, in which the first hydrogenation reactor is operated at inlet temperatures from 170° C. to 190° C.

49. The method according to claim 1, in which the first hydrogenation reactor is operated at pressures from 8 MPa to 10 MPa.

50. The method according to claim 1, in which the catalyst for the second hydrogenation reaction is ruthenium and tin on activated carbon support.

51. The method according to claim 1, in which the catalyst metal loading for the second hydrogenation reaction is 1% to 10% with tin to ruthenium ratio of 5% tin and 7% ruthenium.

52. The method according to claim 1, in which the second hydrogenation reactor is operated at inlet temperatures from 230° C. to 240° C.

53. The method according to claim 1, in which the CHDA concentration in the first hydrogenation reactor product is maintained at 30% to 40% by weight.

54. The method according to claim 1, in which water used as solvent is only 1 to 2.5 times the TPA feed by weight.

* * * * *